United States Patent
Klauber et al.

(10) Patent No.: US 10,087,133 B2
(45) Date of Patent: Oct. 2, 2018

(54) PROCESS FOR PROVIDING DIHALOGEN SUBSTITUTED SALICYLIC ACID DERIVATIVES

(71) Applicant: BASF SE, Ludwigshafen (DE)

(72) Inventors: Eric George Klauber, Bad Duerkheim (DE); Michael Rack, Eppelheim (DE); Thomas Zierke, Boehl-Iggelheim (DE); Nicole Holub, Mannheim (DE); David Cortes, Quincy, IL (US); Gerald Schmelebeck, Buna, TX (US); Junmin Ji, Beaumont, TX (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/102,353

(22) PCT Filed: Dec. 10, 2014

(86) PCT No.: PCT/EP2014/077266
§ 371 (c)(1),
(2) Date: Jun. 7, 2016

(87) PCT Pub. No.: WO2015/086698
PCT Pub. Date: Jun. 18, 2015

(65) Prior Publication Data
US 2016/0311747 A1    Oct. 27, 2016

Related U.S. Application Data

(60) Provisional application No. 61/914,399, filed on Dec. 11, 2013.

(30) Foreign Application Priority Data

Jan. 7, 2014   (EP) .................................... 14150312

(51) Int. Cl.
| | | |
|---|---|---|
| *C07C 51/367* | (2006.01) | |
| *C07C 67/31* | (2006.01) | |
| *C07C 45/64* | (2006.01) | |
| *C07C 253/30* | (2006.01) | |
| *C07C 51/08* | (2006.01) | |

(52) U.S. Cl.
CPC ............ *C07C 51/367* (2013.01); *C07C 45/64* (2013.01); *C07C 51/08* (2013.01); *C07C 67/31* (2013.01); *C07C 253/30* (2013.01)

(58) Field of Classification Search
None
See application file for complete search history.

(56) References Cited

U.S. PATENT DOCUMENTS

| | | |
|---|---|---|
| 2,799,714 A | 7/1957 | Dugan |
| 3,013,054 A | 12/1961 | Richter |
| 3,399,034 A | 8/1968 | Genas |
| 3,726,929 A | 4/1973 | Milnes |
| 4,005,151 A | 1/1977 | Wataya |
| 4,094,913 A | 6/1978 | Carlson |
| 4,161,611 A | 7/1979 | Kim |
| 4,232,172 A | 11/1980 | Becher |

FOREIGN PATENT DOCUMENTS

| | | |
|---|---|---|
| CN | 102125035 A | 7/2011 |
| CN | 102295552 A | 12/2011 |
| CN | 102516072 | 6/2012 |
| CN | 102838457 A | 12/2012 |
| DE | 2509407 A1 | 9/1975 |
| DE | 3512877 C1 | 11/1986 |
| GB | 1404435 A | 8/1975 |
| JP | 1149715 A2 | 6/1989 |
| WO | 200183417 A1 | 11/2001 |
| WO | 2015049160 A1 | 4/2015 |
| WO | 2015049360 A1 | 4/2015 |
| WO | 2015067494 A1 | 5/2015 |
| WO | 2015082415 A1 | 6/2015 |
| WO | 2015082422 A2 | 6/2015 |
| WO | 2015086698 A1 | 6/2015 |
| WO | 2015095284 A1 | 6/2015 |
| WO | 2015124651 A1 | 8/2015 |

OTHER PUBLICATIONS

Office Action, issued in corresponding CN Application No. 201480074645.8, dated 2016.
Shan et al., "Pd-Catalyzed C-H Oxygenation with TFA/TFAA: Expedient Access to Oxygen-Containing Heterocycles and Late-Stage Drug Modification," Angew. Chem. Int. Ed., vol. 51, (2012), pp. 13070-13074.
Verloop et al., "Use of Linear Free Energy Related and Other Parameters in the Study of Fungicidal Selectivity," Pesticide Science, vol. 7, No. 4, (1976), pp. 379-390.
Li et al., "Pd(OAc)2-Catalyzed Alkoxylation of Arylnitriles via sp2 C-H Bond Activation Using Cyano as the Directing Group," The Journal of Organic Chemistry, vol. 77, No. 18, (2012), pp. 8362-8366.
Zhang et al., "Pd(II)-Catalyzed Hydroxylation of Arenes with 1 atm of O2 or Air," Journal of the American Chemical Society, vol. 131, No. 41, (2009), pp. 14654-14655.
International Search Report, issued in PCT/EP2014/077266, dated Feb. 19, 2015.
International Preliminary Report on Patentability, issued in PCT/EP2014/077266, dated Jun. 14, 2016.
Finger et al., "Aromatic Fluorine Compounds. VIII. Plant Growth Regulators and Intermediates," Journal of the American Chemical Society, vol. 81, (1959), pp. 94-101.

(Continued)

*Primary Examiner* — Clinton A Brooks
*Assistant Examiner* — Jennifer C Sawyer
(74) *Attorney, Agent, or Firm* — Brinks Gilson & Lione

(57) ABSTRACT

The present invention relates to a process for providing dihalogen substituted salicylic acid derivatives of formula (II):

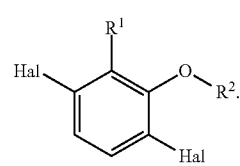

7 Claims, No Drawings

(56) References Cited

OTHER PUBLICATIONS

Holleman, M.A.F., "Les trois trichorobenzenes et leur reaction avea le methylate de sodium", Recueil des travaux chimiques des pays-bas et de la belique, 1918, p. 195-204, vol. 37.

Testaferri, L., et al., "The reactions of unactivated aryl halides with sodium methoxide in HPMA", Tetrahedron, 1983, p. 193-197, vol. 29, No. 1.

Kraay, G.M. "L'action du methylate de sodium sur quelques derivres de l'orthodichlorobenzene" Recueil des travaux chimiques des pays-bas, Elsevier Science Publishers, Jan. 1931, p. 753-792, vol. 50.

Smith, M.S. et al., "March's Advanced Organic Chemistry" 5th Edition, 2001, p. 860-861, John Wiley & Sons, Inc., New York, USA.

Noelting et al., "Zur Kenntniss des Amido-p-dichlorbenzols," Berichte der Deutschen Chemischen Gesellschaft, (1905), p. 3506.

Cresp et al., "Synthesis of Piloquinone, a Metabolite of Streptomyces Pilosus Ettlinger," Journal of the Chemical Society, 1974, pp 2435-2447.

Schmitz et al., "Ortho-Specific Bromination of Phenols," Journal für praktische Chemie, 1985, vol. 327, No. 6, pp. 998-1006.

Decrauw, TH. "The principle of induced alternating polarity in connection with the reacions of derivatives of p-dichlorobenzene and other compounds with sodium methylate", Recueil des travaux chimiques des pays-Bas, Elsevier science Publishes. Amerdam, NL, Jan. 1, 1931, vol. 50, p. 753-792.

Ouellet, S. et al., "Regioselective SNAr reactions of substituted diflourobenzene derivatives: practical synthesis of fluoroaryl ethers and substituted resorcinols", Tetrahedron Letters, Jul. 8, 2009, p. 3776-3779, vol. 50, No. 27.

Li et al., "Preparation of Monofluorophenols via the Reaction of Difluorobenzene Derivatives with Potassium Trimethylsilanoate," SynLett, vol. 2009, No. 4, (2009), pp. 633-637.

Lin et al., "Synthesis of Chlorinated and Non-Chlorinated Biphenyl-2,3- and 3,4-catechols and Their [2H3]-isotopomers," Org. Biomol. Chem., vol. 2, (2004), pp. 2624-2629.

Hashimoto et al., "Hydrolysis of 1,2,4-Trichlorobenzene," The Doshisha Engineering Review, vol. 8, No. 2, (1957), pp. 76-79.

Methoxide Catalysts in Biodiesel Production, (2012), retrieved from http://articles.extension.org/pages/26615/methoxide-catalysts-in-biodiesel-production, pp. 1-3.

Office Action, issued in co-pending U.S. Appl. No. 15/026,878, dated Jan. 9, 2017.

Final Office Action, issued in co-pending U.S. Appl. No. 15/026,878, dated May 24, 2017.

Office Action, issued in co-pending U.S. Appl. No. 15/311,951, dated Jul. 26, 2017.

Office Action, issued in co-pending U.S. Appl. No. 15/026,878, dated Dec. 11, 2017.

Holleman, "Les Trois Trichlorobenzenes et Leur Reactoin avec le Methylate de Sodium," Recueil des Travaux Chimiques des Pays-Bas et de la Belique, vol. 37, (1918), pp. 195-204 (XP-002723298).

PROCESS FOR PROVIDING DIHALOGEN SUBSTITUTED SALICYLIC ACID DERIVATIVES

This application is a National Stage application of International Application No. PCT/EP2014/077266, filed Dec. 10, 2014, which claims the benefit of U.S. Provisional Application No. 61/914,399, filed Dec. 11, 2013. This application also claims priority under 35 U.S.C. § 119 to European Patent Application No. 14150312.8, filed Jan. 7, 2014.

The present invention relates to a process for providing dihalogen substituted salicylic acid derivatives. In a preferred embodiment, the present invention provides an improved process for the production of the herbicide dicamba (3,6-dichloro-2-methoxybenzoic acid).

BACKGROUND OF THE INVENTION

Dicamba is a selective herbicide currently used for treating e.g. corn, wheat or grassland. It kills broadleaf weeds before and after they sprout. The trivial name dicamba refers to the compound 3,6-dichloro-2-methoxybenzoic acid. The estimated global demand for dicamba in 2012 was about 12.000 metric tons per year. However, it is expected that the global demand for dicamba will increase significantly.

Dicamba is typically produced on an industrial scale from 2,5-dichlorophenol using carboxylation under Kolbe-Schmitt conditions, methylation and subsequently saponification/acidification. 2,5-Dichorophenol in turn can be obtained from 1,4-dichlorobenzene or 1,2,4-trichlorobenzene. The synthetic route via 1,4-dichlorobenzene involves nitration and subsequent diazotation, and, therefore is undesired for use on an industrial scale. The synthetic route via 1,2,4-trichlorobenzene suffers from limited availability of this starting material and from the formation of several byproducts which are formed in the synthesis of 2,5-dichlorophenol.

In order to meet the increasing market demand for compounds such as dicamba, there is a need in the art for alternative processes, involving a reduced number of steps and/or improved yield, for providing dihalogen substituted salicylic acid derivatives, especially including dicamba.

The object of the present invention is to meet the above needs. It is a further object of the present invention to implement the improved process for the synthesis of dicamba on an industrial scale. A further object of the present invention is the provision of a cost effective process for the synthesis of dicamba.

Even minor improvements in the yield in reaction sequences for obtaining dicamba would provide a tremendous benefit. For example, an improvement of yield of 1% would provide an additional annual amount 120 metric tons of dicamba.

SUMMARY OF THE INVENTION

The present invention relates to an improved process for providing dihalogen substituted salicylic acid derivatives involving ortho-alkoxylation or ortho-hydroxylation of dihalogen substituted benzoic acid derivatives or benzonitrile derivatives using transition metal catalyzed oxidation, such as Pd(II) catalysis. In particular, the present invention relates to a process for providing a compound of formula (II):

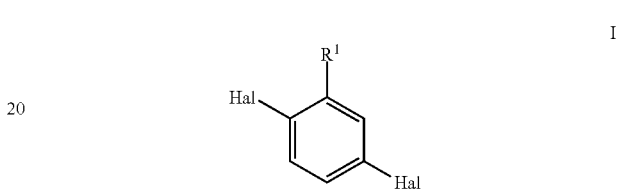

wherein $R^1$ is —CN, —COOH or —COR$^3$, $R^2$ is —($C_1$-$C_4$) alkyl or hydrogen, $R^3$ is —O($C_1$-$C_4$)alkyl, —($C_1$-$C_4$)alkyl or —($C_6$-$C_{10}$)aryl, and Hal is independently selected from —F, —Cl, —Br, or —I, the process comprising the step of:
Reacting a compound of formula (I)

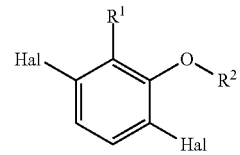

wherein $R^1$ and Hal are defined as above, in the presence of a transition metal catalyst. In a preferred embodiment, the catalysts is a transition metal catalyst, such as a Pd(II) catalyst.

In one preferred embodiment of the present invention, the process involves ortho-alkoxylation of benzonitrile derivatives. These embodiments relate to a process as defined above, wherein $R^1$ is —CN, and $R^2$ is —($C_1$-$C_4$)alkyl. In these embodiments the step of reacting the compound of formula (I) is carried out in the further presence of an alcohol of formula HOR$^2$ and preferably of an oxidant such as $Na_2S_2O_8$. The compounds of formula (II) in which $R^1$ is —CN, and $R^2$ is —($C_1$-$C_4$)alkyl

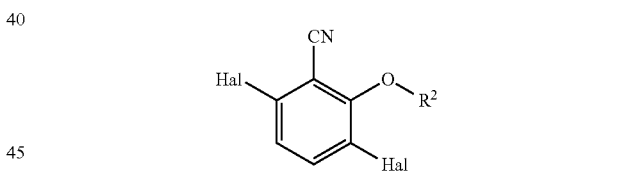

can be converted to compounds of formula (II) in which $R^1$ is —COOH

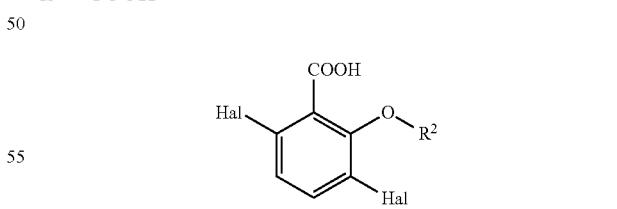

wherein $R^2$ is —($C_1$-$C_4$)alkyl, and Hal is as defined above.

In an alternative embodiment, the process involves ortho-hydroxylation of benzoic acid derivatives. These alternative embodiments relate to a process as defined above, wherein $R^1$ is —COOH, and $R^2$ is hydrogen, and the step of reacting the compound of formula (I) is carried out in the presence of an oxidizing agent such as molecular oxygen ($O_2$). The compounds of formula (II) in which $R^1$ is —COOH and $R^2$ is hydrogen

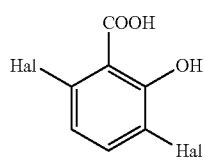

can be converted to compounds of formula (II)

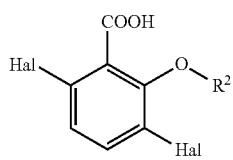

wherein $R^2$ is —$(C_1$-$C_4)$alkyl, and Hal is independently as defined above.

In a further alternative embodiment, the process involves ortho-hydroxylation of benzoic acid esters or ketones. The alternative embodiments relate to processes as defined above, wherein $R^1$ is —$COR^3$, wherein $R^3$ is as defined above, and $R^2$ is hydrogen, and the step of reacting the compound of formula (I) is carried out in the further presence of an oxidant and a carboxylic acid and a corresponding anhydride. These alternative embodiments relate to a process as defined above, preferably further comprising the step of:

Reacting a compound of formula (II) in which $R^1$ is —$COR^3$ and $R^3$ is as defined above, and $R^2$ is hydrogen

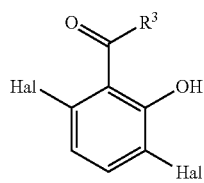

to obtain a compound of formula (II)

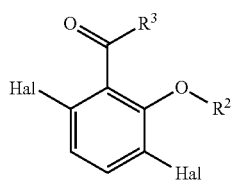

wherein $R^2$ is —$(C_1$-$C_4)$alkyl, and Hal is independently selected from —F, —Cl, —Br, or —I.

The compounds of formula (II) in which $R^1$ is —$COR^3$ and $R^3$ is as defined above, and $R^2$ is —$(C_1$-$C_4)$alkyl

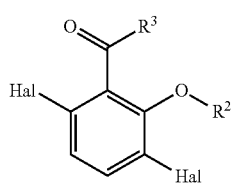

can be converted to compounds of formula (II)

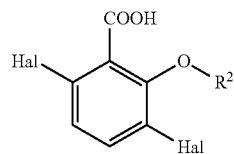

wherein $R^1$ is —COOH, and Hal is independently selected from —F, —Cl, —Br, or —I.

In preferred embodiments of the present invention, $R^2$ is selected from hydrogen, methyl and ethyl, more preferably methyl.

In a preferred embodiment of the present invention, the transition is selected from a Pd(II), Ru(II), Rh(II), Cu(II), or Fe(II) catalyst. More preferably, a Pd(II) catalyst is selected as the transition metal catalyst. Even more preferably, Pd(OAc)$_2$ is used as the Pd(II) catalyst in the step of reacting a compound of formula (I) to obtain a compound of formula (II).

In particular preferred embodiments, the processes according to the present invention are employed in the synthesis of dicamba. In these preferred embodiments, the compound of formula (II) is

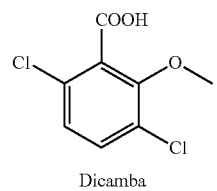

Dicamba

Further preferred embodiments of the present invention are apparent from the following detailed description and the attached claim set.

DETAILED DESCRIPTION OF THE INVENTION

In the following, illustrative embodiments of the present invention are described in more detail.

The term "Hal" or "halogen" when used in the context of the present invention refers to —F, —Cl, —Br or —I. Preferably, the halogen is —Cl or —Br, more preferably —Cl.

The term "OAc" refers in the context of the present invention to an acetate ion —O(O)C—CH$_3$. The term "TFA" means according to the present invention trifluoroacetic acid. In the context of the present invention, the term "TFAA" refers to trifluoroacetic anhydride. The term "acac" means acetylacetate. The term "PPh$_3$" means triphenylphosphine.

The term "transition metal catalyst" refers in the context of the present invention to a catalyst comprising Pd(II), Ru(II), Rh(II), Cu(II), or Fe(II).

The present invention relates to a process of ortho-alkoxylation or ortho-hydroxylation of dihalogen substituted benzonitrile, benzoic acid derivatives, benzoic acid esters or corresponding ketones in the presence of a transition metal catalyst such as a Pd(II) catalyst. The Pd(II) catalyst may be selected from Pd(OAc)$_2$, Pd(TFA)$_2$, PdCl$_2$(CH$_3$CN)$_2$, Pd(a- cac)$_2$ or PdCl$_2$(PPh$_3$)$_2$. Preferably, Pd(OAc)$_2$ is employed in the present invention as the Pd(II) catalyst.

Alkoxylation of Dihalogen Substituted Benzonitriles

In one embodiment, the present invention relates to a process of ortho-alkoxylating 2,5-dihalogen substituted benzonitriles in the presence of a transition metal catalyst such as a Pd(II) catalyst (e.g. Pd(OAc)), wherein R$^2$ is —(C$_1$-C$_4$) alkyl and Hal is as defined above.

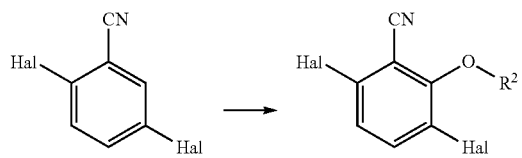

Illustrative reaction conditions are e.g. described in W. Li et al., J. Org. Chem. 2012, 77, 8362-8366. The reaction according to this embodiment of the present invention is typically carried out in the presence of an alcohol of the formula HO—R$^2$, wherein R$^2$ is as defined above. In one embodiment, the alcohol of formula HO—R$^2$, in addition to undergoing a reaction, serves as a solvent. The alcohol HO—R$^2$ may be the only solvent present in the reaction. In other embodiments, a co-solvent in addition to the alcohol of formula HO—R$^2$ is present. Suitable co-solvents include organic solvents, preferably selected from dioxane, 1,2-dichloroethane (DCE), acetonitrile, dimethylsulfoxide (DMSO), N,N-dimethylformamide (DMF), or N-methylpyrrolidone (NMP). In preferred embodiments, no co-solvent is used so that the alcohol of formula HO—R$^2$ is both a reactant and the solvent. In a further preferred embodiment, the alcohol of formula HO—R$^2$ as well as any co-solvent, if present, is used in anhydrous form.

In preferred embodiments, the alcohol of formula HO—R$^2$ is present in an amount of about 2 to about 4 liter, based on one mol of the compound of formula (I). More preferably, the alcohol of formula HO—R$^2$ is present in the reaction in an amount of about 2.5 to about 3.5 liter per one mol of the compound of formula (I), such as 3 liter per one mol of the compound of formula (I).

As outlined above, the presence of a transition metal catalyst such as a Pd(II) catalyst is an essential requirement according to the present invention. The amount of e.g. the Pd(II) catalyst present in the reaction is preferably about 0.05 molar equivalents to about 0.2 molar equivalents per one equivalent of the compound of formula (I). More preferably, about 0.08 to about 0.12 molar equivalents, most preferably about 0.1 molar equivalent, of the catalyst are used per one molar equivalent of the compound of formula (I). The preferred Pd(II) catalyst to be employed according to the present invention is Pd(OAc)$_2$.

The above reaction is preferably carried out in the additional presence of an oxidant. Suitable oxidants may be selected from K$_2$S$_2$O$_8$, Na$_2$S$_2$O$_8$, O$_2$, or a peroxyacetic acid ester, such as peroxyacetic acid tert-butyl ester. In a preferred embodiment, Na$_2$S$_2$O$_8$ is used as an oxidant. Furthermore, the oxidant is preferably present in an amount of about 4 to about 6 molar equivalents per one molar equivalent of the compound of formula (I). More preferably, the oxidant is present in an amount of about 4.5 to about 5.5 molar equivalents per one molar equivalent of the compound of formula (I). Most preferably, the oxidant is present in an amount of about 5 molar equivalents per one molar equivalent of the compound of formula (I).

The reaction can be carried out at a temperature ranging from about 20° C. to the boiling point of the solvent or solvent mixture used. In a preferred embodiment, the reaction is carried out at a temperature of about 20° C. to about 70° C. More preferably, the temperature is gradually raised during the reaction. Thus, in a preferred embodiment, the reaction is carried out at about 20° C. to about 25° C. for about 6 to about 10 hours, such as about 8 hours, and then the temperature is raised to about 60° C. to about 70° C. for additional about 14 to about 18 hours, such as about 16 hours.

In a preferred embodiment of this aspect of the present invention, the alkoxylated benzonitrile of formula (II), in which R$^1$ is —CN, R$^2$ is —(C$_1$-C$_4$)alkyl, and Hal is as defined above, is hydrolyzed to obtain the corresponding benzoic acid derivatives of formula (II), wherein R$^1$ is —COOH, and R$^2$ and Hal are as defined above.

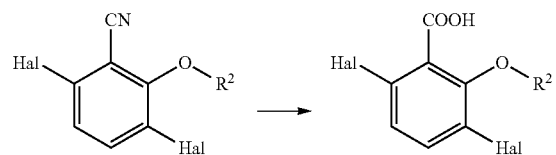

Suitable reaction conditions for the above hydrolysis are known to a person skilled in the art and include hydrolysis in an aqueous base or an aqueous acid. For example, the nitrile of formula (II), wherein R$^1$ is —CN, may be treated with an alkali metal hydroxide such as NaOH, LiOH, or KOH, e.g. 15% NaOH, in water or a water/alcohol mixture such as water and ethanol, at temperatures in the range of about 80° C. to about 105° C. to obtain the corresponding benzoic acid derivative of formula (II), wherein R$^1$ is —COOH. Alternatively, the conversion can be accomplished in an aqueous medium using an acid such as H$_2$SO$_4$ at about 80° C. to about 105° C.

The compounds of formula (I), in which R$^1$ is —CN may be obtained by processes known in the art. For example, about one equivalent of 1,2,4-trihalobenzene as shown below, wherein Hal is as defined above, may be reacted at a temperature of about 200° C. to about 240° C. with about one equivalent of CuCN and about 1 to about 5 equivalents of a tertiary amine having a boiling point which is higher than the reaction temperature (e.g. higher than 200° C.), to obtain the compound of formula (I), in which R$^1$ is —CN. Suitable reaction conditions are e.g. described in DE 2001289.

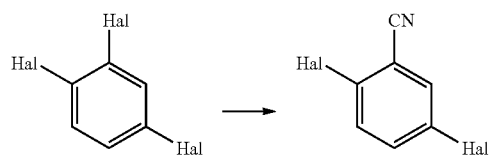

Scheme I shows an overview of the reaction sequence for obtaining 3,6-dihalogen substituted salicylic acid derivatives starting from 1,2,4-trihalogen substituted benzene derivatives according to the above embodiment.

Scheme I:

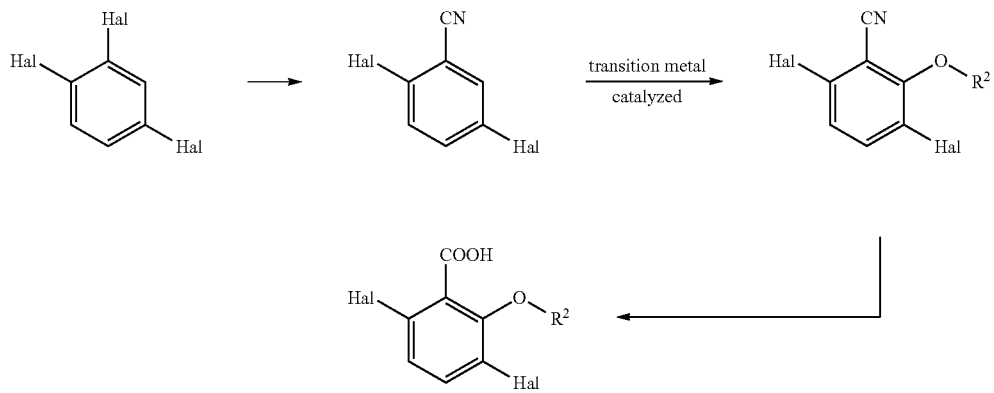

As described above, in preferred embodiments according to the present invention, Hal is —Cl, and $R^2$ is methyl. Thus, in preferred embodiments the present invention provides an improved reaction sequence for obtaining dicamba. In a first step of this reaction sequence, 1,2,4-trichlorobenzene is reacted with CuCN as described above for obtaining 2,5-dichlorobenzonitrile.

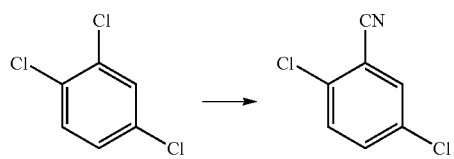

2,5-Dichlorobenzonitrile is a compound according to formula (I) of the present invention in which Hal is —Cl and $R^1$ is —CN. However, it is not mandatory according to this preferred embodiment that 2,5-dichlorobenzonitrile is provided in this way. Rather, it is understood that 2,5-dichlorobenzonitrile irrespective of its method of synthesis can be used for the following reaction step.

In a second step of the reaction sequence for obtaining dicamba, 2,5-dichlorobenzonitrile is ortho-methoxylated under the conditions described above in the presence of methanol to obtain 3,6-dichloro-2-methoxybenzonitrile.

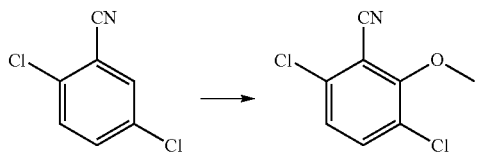

3,6-Dichloro-2-methoxybenzonitrile is a compound according to formula (II) of the present invention in which Hal is —Cl, $R^1$ is —CN, and $R^2$ is methyl.

In a final step of the reaction sequence according to this preferred embodiment, dicamba is obtained by hydrolyzing the nitrile group to the corresponding benzoic acid derivative under conditions as described above.

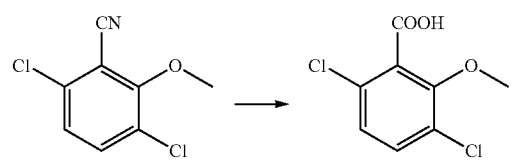

Hydroxylation of Dihalogen Substituted Benzoic Acid Derivatives

In an alternative embodiment, the present invention relates to a process of ortho-hydroxylating 2,5-dihalogen substituted benzoic acid derivatives in the presence of a transition metal catalyst such as a Pd(II) catalyst (e.g. Pd(OAc)$_2$).

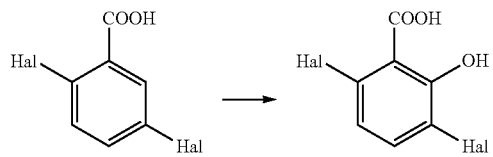

Illustrative reaction conditions are e.g. described in Y.-H-Zhang et al., J. Am. Chem. Soc. 2009, 131, 14654-14655. The reaction according to this embodiment of the present invention is carried out in the further presence of molecular oxygen (O$_2$). The reaction can be carried out by providing O$_2$ or air at atmospheric pressure. The obtained yield may be improved by providing O$_2$ or air at elevated pressure. Thus, in one embodiment, the present invention relates to a process as defined above carried out in the presence of O$_2$ at a pressure of about 101.3 kPa to about 506.6 kPa.

The hydroxylation reaction according to this aspect of the present invention is typically carried out in solution in the presence of a solvent. Suitable solvents include organic solvents, preferably selected from dioxane, 1,2-dichloroethane (DCE), acetonitrile, dimethylsulfoxide (DMSO), dimethylformamide (DMF), N-methylpyrrolidone (NMP), N,N-dimethylacetamide (DMA), N,N-dimethylpropionamide (DMP), or any mixtures thereof, preferably DMF, DMA, DMP, or any mixtures thereof.

As outlined above, the presence of a transition metal catalyst such as a Pd(II) catalyst is also an essential requirement according to this aspect of the present invention. The amount of e.g. the Pd(II) catalyst present in the reaction is preferably about 0.05 equivalents to about 0.2 molar equivalents per one molar equivalent of the compound of formula (I). More preferably, about 0.08 to about 0.12 molar equivalents, most preferably about 0.1 molar equivalent, of e.g. Pd(II) catalyst are used per one molar equivalent of the compound of formula (I). The preferred Pd(II) catalyst according to the present invention is Pd(OAc)$_2$.

The reaction is typically carried out in the presence of a base. Suitable bases are preferably selected from KOAc, NaOAc, K$_2$HPO$_4$, CsOAc, or combinations thereof. Of these bases, KOAc, K$_2$HPO$_4$, CsOAc, or combinations thereof are more preferred. The base is typically present in an amount of about 1 to about 3 molar equivalents per one molar equivalent of the compound of formula (I). More preferably, the base is present in an amount of about 1.5 to about 2.5 molar equivalents, such as about 2 molar equivalents, per one molar equivalent of the compound of formula (I).

The above reaction may be carried out in the presence of an oxidant, although the presence of an oxidant is not crucial according to this aspect of the invention. A suitable oxidant according to this aspect of the invention is e.g. benzoquinone. The oxidant such as benzoquinone may be present in an amount of about 0.2 to about 1 molar equivalent per one molar equivalent of the compound of formula (I). Typically, the yields are increased in the presence of an oxidant such as benzoquinone.

The reaction can be carried out at a temperature ranging from about 20° C. to the boiling point of the solvent or solvent mixture used. In a preferred embodiment, the reaction is carried out at a temperature of about 20° C. to about 150° C. More preferably, the temperature is carried out at elevated temperature such as about 80° C. to about 150° C., more preferably about 100° C. to about 130° C.

In a preferred embodiment of this aspect of the present invention, the hydroxylated benzoic acid derivative of formula (II), in which R$^1$ is —COOH, R$^2$ is hydrogen, and Hal is as defined above, is converted to a corresponding ether of formula (II), wherein R$^1$ is —COOH, R$^2$ is —(C$_1$-C$_4$)alkyl, and Hal is as defined above

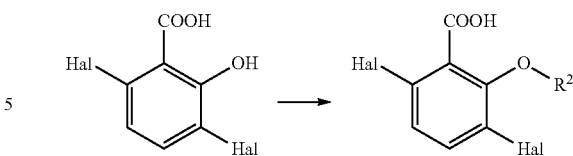

The reaction is accomplished by reacting the compound of formula (II) in which is hydrogen with a (C$_1$-C$_4$)alkyl halide of the formula Y—R$^2$, wherein Y is —Cl, —Br or —I, preferably —Cl or —Br, more preferably —Cl, and R$^2$ is —(C$_1$-C$_4$)alkyl. In a preferred embodiment, the alkyl halide is methyl chloride. The reaction can be carried out in aqueous solution. During the reaction, the pH, temperature and pressure may be controlled such that the reaction is carried out at a pH of 8-12, a temperature of about 80° C. to about 100° C. and a pressure of about 500 to about 1050 kPa. An excess of alkyl halide is typically used.

The compounds of formula (I), in which R$^1$ is —COOH, may be obtained by processes known in the art, e.g. by means of hydrolyzing the nitrile group of compounds of formula (I), in which R$^1$ is —CN, as described above. Suitable reaction conditions for hydrolyzing the nitrile group to obtain benzoic acid derivatives are described above in connection with hydrolyzation of nitrile compounds of formula (II).

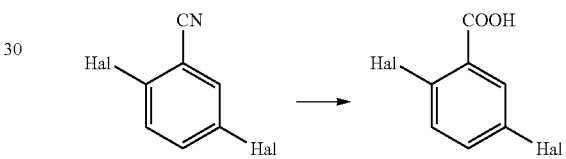

Scheme II shows an overview of the reaction sequence for obtaining 3,6-dihalogen substituted salicylic acid derivatives starting from 1,2,4-trihalogen substituted benzene derivatives according to the above embodiment.

Scheme II:

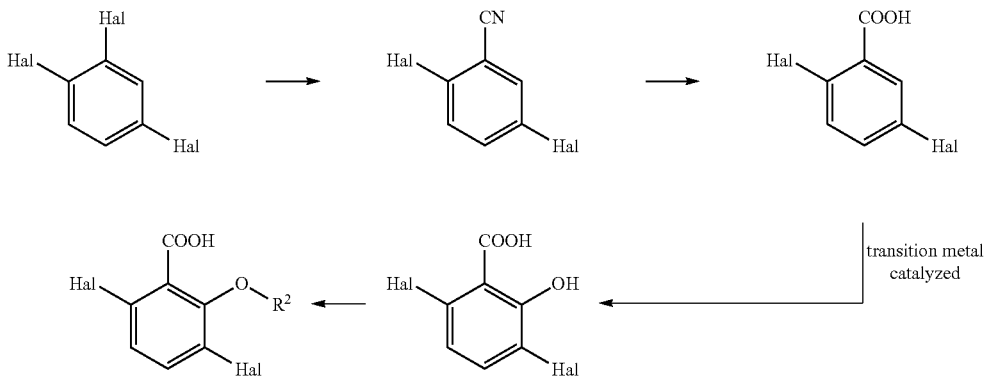

As described above, in preferred embodiments according to the present invention, Hal is —Cl, and R$^2$ is methyl. Thus, in preferred embodiments the present invention provides an improved reaction sequence according to the second aspect for obtaining dicamba. In a first step of said reaction sequence according to the second aspect, 1,2,4-trichlorobenzene is reacted with CuCN as described above for obtaining 2,5-dichlorobenzonitrile.

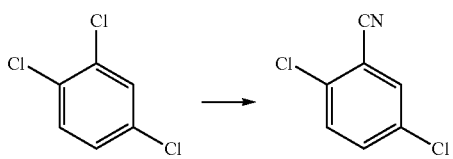 [SMILES: Clc1ccc(Cl)c(Cl)c1 ; N#Cc1cc(Cl)ccc1Cl]

2,5-Dichlorobenzonitrile is a compound according to formula (I) of the present invention in which Hal is —Cl and $R^1$ is —CN. However, it is not mandatory according to this preferred embodiment that 2,5-dichlorobenzonitrile is provided in this way. Rather, it is understood that 2,5-dichlorobenzonitrile irrespective of its method of synthesis can be used for the following reaction step.

In a second step of the reaction sequence for obtaining dicamba according to this aspect of the invention, 2,5-dichlorobenzonitrile is hydrolyzed to the corresponding benzoic acid derivative under conditions as described above to obtain 2,5-dichlorobenzoic acid.

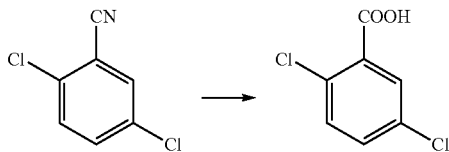 [SMILES: N#Cc1cc(Cl)ccc1Cl ; O=C(O)c1cc(Cl)ccc1Cl]

2,5-Dichlorobenzoic acid is a compound of formula (I) according to the invention in which $R^1$ is —COOH and Hal is —Cl.

In a third step of the reaction sequence for obtaining dicamba according to the second aspect of the invention, 2,5-dichlorobenzoate is ortho-hydroxylated under the conditions described above in the presence of molecular oxygen ($O_2$) to obtain 3,6-dichloro-2-hydroxybenzoic acid.

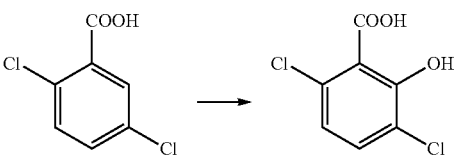 [SMILES: O=C(O)c1cc(Cl)ccc1Cl ; O=C(O)c1c(Cl)ccc(Cl)c1O]

3,6-Dichloro-2-hydroxybenzoic acid is a compound according to formula (II) of the present invention in which Hal is —Cl, $R^1$ is —COOH, and $R^2$ is hydrogen.

In a final step of the reaction sequence according to this preferred embodiment, dicamba is obtained by methylating the hydroxyl group of 3,6-dichloro-2-hydroxybenzoic acid under conditions as described above.

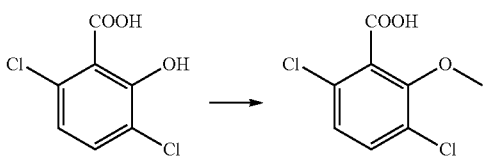

Hydroxylation of Dihalogen Substituted Benzoic Acid Esters or Phenylketones

In a further alternative embodiment, the present invention relates to a process of ortho-hydroxylating 2,5-dihalogen substituted benzoic acid esters or phenylketones in the presence of a transition metal catalyst. Preferred catalysts in this respect include e.g. a Rh(II), Ru(II) or Pd(II) catalyst (e.g. Pd(OAc)$_2$). In compounds of formula (I) suitable for this alternative, $R^1$ is —COR$^3$, wherein $R^3$ is as defined above.

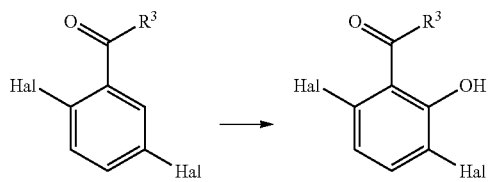

The step of reacting the compound of formula (I) is carried out in the further presence of an oxidant and a carboxylic acid and a corresponding anhydride. Illustrative reaction conditions are e.g. described in G. Shan et al., Angew. Chem. Int. Ed. 2012, 51, 13070-13074; Y. Yang et al., Org. Lett., Vol. 14, No. 11, 2012; or G. Shan et al., Org. Biomol. Chem., 2013, 11, 2318-2322.

Preferred examples of —(C$_1$-C$_4$)alkyl in —O(C$_1$-C$_4$) alkyl or —(C$_1$-C$_4$)alkyl of $R^3$ include methyl and ethyl. Preferred examples of —(C$_6$-C$_{10}$)aryl in $R^3$ include phenyl.

The reaction according to this embodiment of the present invention is carried out in the further presence of an oxidant. Suitable oxidants may be selected from K$_2$S$_2$O$_8$, Na$_2$S$_2$O$_8$, KIO$_4$, NaIO$_4$, HIO$_3$, bis(acetoxy)iodobenzene (PhI(OAc)$_2$), or H$_2$O$_2$. In a preferred embodiment, K$_2$S$_2$O$_8$, or PhI(OAc)$_2$ is used as the oxidant. Furthermore, the oxidant is preferably present in an amount of about 1 to about 3 molar equivalents per one molar equivalent of the compound of formula (I). More preferably, the oxidant is present in an amount of about 1.1 to about 2.0 molar equivalents per one molar equivalent of the compound of formula (I).

The hydroxylation reaction according to this aspect of the present invention is carried out in solution in an acidic medium comprising a carboxylic acid and a corresponding anhydride. Suitable carboxylic acids and corresponding anhydrides include trichloroacetic acid and trichloroacetic anhydride (TCA/TCAA), or trifluoroacetic acid and trifluoroacetic anhydride (TFA/TFAA). In a preferred embodiment, TFA/TFAA is used. The ratio of carboxylic acid, such as TFA, to the corresponding anhydride, such as TFAA, is preferably 5:1 to 13:1, more preferably 8:1 to 10:1.

As outlined above, the presence of a transition metal catalyst such as a Rh(II), Ru(II) or Pd(II) catalyst is also an essential requirement according to this aspect of the present invention. Examples of preferred Ru(II) catalysts include [RuCl$_2$(p-cymene)]$_2$, RuCl$_2$(PPh)$_3$ and Ru(CO)HCl(PPh)$_3$. Examples of preferred Rh(II) catalysts include Rh$_2$(OAc)$_4$. Examples of preferred Pd(II) catalysts include (Pd(OAc)$_2$. The amount of the transition metal catalyst present in the reaction depends on the transition metal applied. The amount is preferably about 0.01 molar equivalents to about 0.25 molar equivalents per one molar equivalent of the compound of formula (I). Typically, Ru(II) catalysts are applied in an amount of about 0.01 to about 0.03 molar equivalents, Rh(II) catalysts are applied in an amount of about 0.04 to about 0.06 molar equivalents, Pd(II) catalysts are applied in an amount about 0.04 to about 0.12 molar equivalents per one molar equivalent of the compound of formula (I).

The reaction can be carried out at a temperature ranging from about 20° C. to the boiling point of the carboxylic acid and corresponding anhydride used as a solvent system. In a preferred embodiment, the reaction is carried out at a temperature of about 20° C. to about 100° C. More preferably, the temperature is carried out at a temperature of about 70° C. to about 100° C.

In a preferred embodiment of this aspect of the present invention, the hydroxylated benzoic acid ester or phenylketone of formula (II), in which $R^1$ is —$COR^3$, $R^3$ is as defined above, $R^2$ is hydrogen, and Hal is as defined above, is converted to a corresponding ether of formula (II), wherein $R^3$ is as defined above, $R^2$ is —($C_1$-$C_4$)alkyl, and Hal is as defined above.

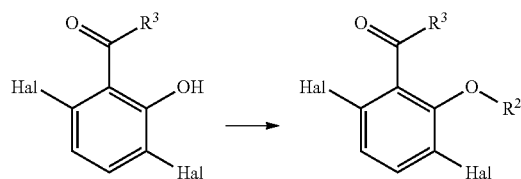

The reaction is accomplished by reacting the above compound of formula (II) in which $R^2$ is hydrogen with a ($C_1$-$C_4$)alkyl halide of the formula Y—$R^2$, wherein Y is —Cl, —Br or —I, preferably —Cl or —Br, more preferably —Cl, and $R^2$ is —($C_1$-$C_4$)alkyl. In a preferred embodiment, the alkyl halide is methyl chloride. The reaction can be carried out in aqueous solution. During the reaction, the pH, temperature and pressure may be controlled such that the reaction is carried out at a pH of about 8 to about 12, a temperature of about 80° C. to about 100° C. and a pressure of about 500 to about 1050 kPa. An excess of alkyl halide is typically used.

HCl or $H_2SO_4$ at elevated temperature. Alternatively, the compound of formula (I), in which $R^1$ is —COOH, may be reacted with a —($C_1$-$C_4$)alkyl halide, such as methyl chloride, in the presence of a base, such as an alkali metal hydroxide e.g. KOH, at room temperature to elevated temperature.

The benzoic acid esters of formula (II), in which $R^1$ is —$COR^3$, and $R^3$ is —O($C_1$-$C_4$)alkyl, obtained as described in detail above, can be converted to compounds of formula (II), in which $R^1$ is —COOH under basic conditions using a suitable base. For example, alkali metal hydroxides such as NaOH may be employed here.

Scheme III shows an overview of the reaction sequence for obtaining 3,6-dihalogen substituted salicylic acid derivatives starting from 2,5-dihalogen substituted benzoic acid esters according to the above embodiment.

Scheme III:

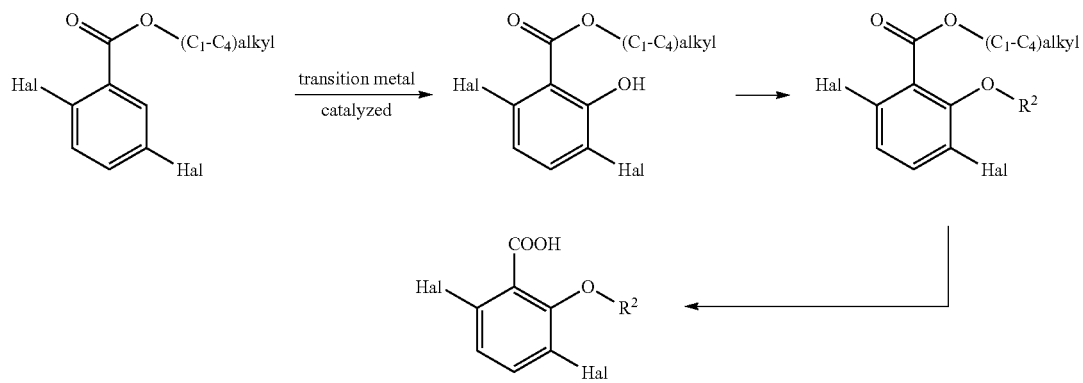

The compounds of formula (I), in which $R^1$ is —$COR^3$, may be obtained by processes known in the art. In one embodiment, benzoic acid ester derivatives of formula (I), in which $R^1$ is —$COR^3$, and $R^3$ is —O($C_1$-$C_4$)alkyl, are obtained by means of esterification the —COOH group of the above-described compounds of formula (I), in which $R^1$ is —COOH. The reaction can be carried out by reacting the compound of formula (I), in which $R^1$ is —COOH, with an alcohol HO—($C_1$-$C_4$)alkyl in the presence of an acid such as In another embodiment, phenylketones of formula (I), in which $R^1$ is —$COR^3$, and $R^3$ is —($C_1$-$C_4$)alkyl or —($C_6$-$C_{10}$)aryl, are obtained by means of Friedel-Crafts acylation of 1,4-dihalobenzene. The reaction can be carried out by reaction 1,4-dihalobenzene with $XCOR^3$, wherein X is —Cl, —Br, —OC(O)$R^3$, or —OH, and $R^3$ is —($C_1$-$C_4$)alkyl or —($C_6$-$C_{10}$)aryl, in the presence of a Lewis acid such as $AlCl_3$.

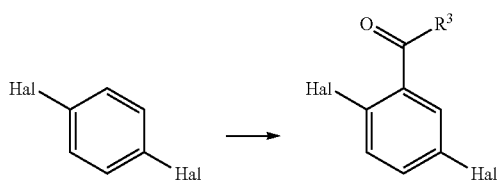

Subsequently, phenylketones of formula (I), in which $R^1$ is —$COR^3$, and $R^3$ is —($C_1$-$C_4$)alkyl or —($C_6$-$C_{10}$)aryl, are subjected to transition metal catalyzed ortho-hydroxylation as described in detail above. The resulting phenylketones of formula (II), in which $R^1$ is —$COR^3$, $R^3$ is —($C_1$-$C_4$)alkyl or —($C_6$-$C_{10}$)aryl, and $R^2$ is hydrogen, are transferred into the corresponding ethers, in which $R^2$ is —($C_1$-$C_4$)alkyl, as described in detail above, and can then be converted to benzoic acid derivatives of formula (II), in which $R^1$ is —COOH, by means of either a haloform reaction and therefore treatment with $Cl_2/I_2/Br_2$ in the presence of a base such as NaOH or KOH or by means of a Baeyer-Villiger-Oxidation and treatment with peroxide equivalents such as peracetic acid, $H_2O_2/H_2SO_4$, meta-chloroperbenzoic acid

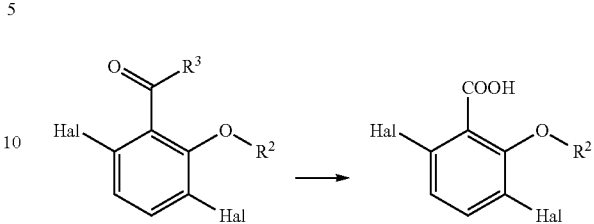

Scheme IV shows an overview of the reaction sequence for obtaining 3,6-dihalogen substituted salicylic acid derivatives starting from 2,5-dihalogen substituted phenylketones according to the above embodiment.

Scheme IV:

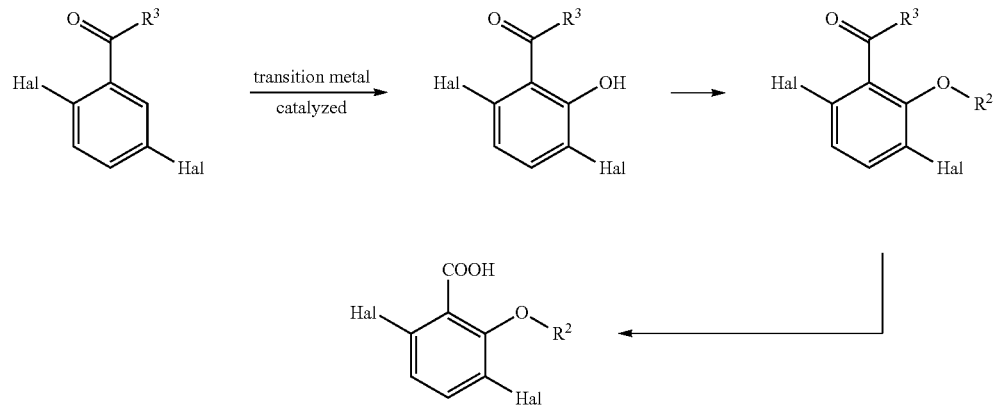

As described above, in preferred embodiments according to the present invention, Hal is —Cl, and $R^2$ is methyl. Thus, in preferred embodiments the present invention provides an improved reaction sequences according to the third aspect for obtaining dicamba. A specific embodiment of a reaction sequence for obtaining dicamba according to the third aspect of the invention starting from 1,4-dichlorobenzene is shown below.

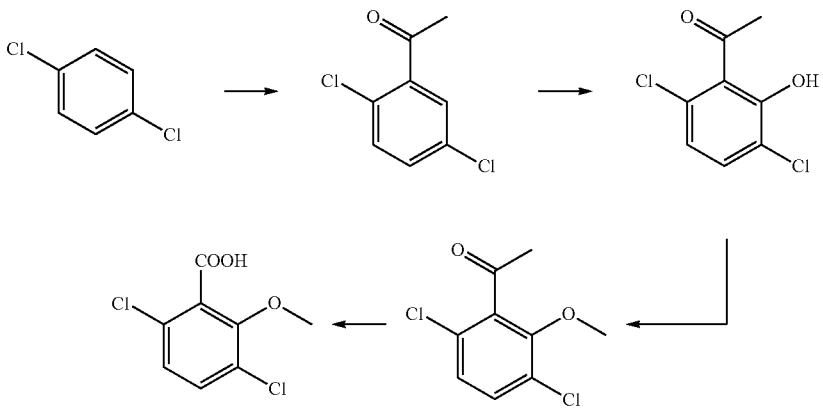

In addition, another specific embodiment for obtaining dicamba according to the third aspect from 2,5-dichlorobenzoic acid methyl ester is illustrated in the following.

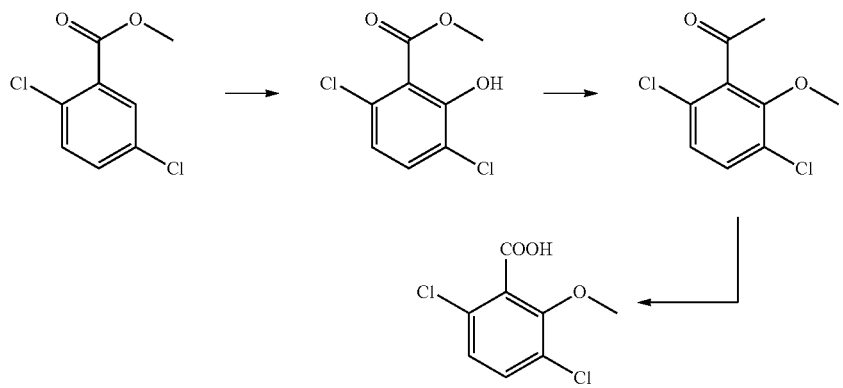

The invention claimed is:

1. A process for preparing a compound of formula (II):

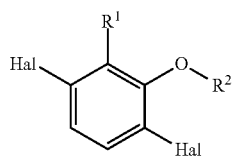

wherein $R^1$ is —COOH,
$R^2$ is —($C_1$-$C_4$)alkyl or hydrogen, and each Hal is Cl
the process comprising the step of:
reacting a compound of formula (I)

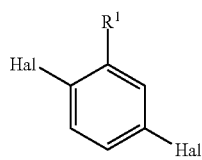

wherein $R^1$ and Hal are defined as above,
in the presence of a transition metal catalyst to a compound of formula (II).

2. The process of claim 1, wherein the transition metal catalyst is a catalyst comprising Pd(II), Ru(II), Rh(II), Cu(II), or Fe(II).

3. The process of claim 1, wherein $R^2$ is —($C_1$-$C_4$)alkyl, and the step of reacting the compound of formula (I) is carried out in the further presence of an oxidant and an alcohol of formula $HOR^2$.

4. The process of claim 3, wherein the oxidant is selected from the group consisting of $K_2S_2O_8$, $Na_2S_2O_8$, $O_2$ and a peroxyacetic acid ester.

5. The process of claim 4, wherein the oxidant is $Na_2S_2O_8$.

6. The process of claim 1, wherein $R^2$ is hydrogen, and the step of reacting the compound of formula (I) is carried out in the further presence of molecular oxygen.

7. The process of claim 1, wherein the compound of formula (II) is

* * * * *